US006587714B2

(12) United States Patent
Tanida

(10) Patent No.: US 6,587,714 B2
(45) Date of Patent: Jul. 1, 2003

(54) COMPACT TYPE OF LIVING BODY VARIABLE MEASURING DEVICE

(75) Inventor: Daisuke Tanida, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/784,143

(22) Filed: Feb. 16, 2001

(65) Prior Publication Data

US 2001/0018561 A1 Aug. 30, 2001

(30) Foreign Application Priority Data

Feb. 29, 2000 (JP) ........................................ 2000-054113

(51) Int. Cl.[7] ................................................ A61B 5/05
(52) U.S. Cl. ...................................................... 600/547
(58) Field of Search .................. 600/547; 206/736–766, 206/305–306, 403, 404; 361/1

(56) References Cited

U.S. PATENT DOCUMENTS

| | | |
|---|---|---|
| 4,949,727 A | 8/1990 | Yamazaki et al. |
| 5,043,888 A * | 8/1991 | Uriarte .................. 364/413.12 |
| 6,122,152 A * | 9/2000 | Goto et al. ..................... 361/1 |
| 6,243,651 B1 * | 6/2001 | Masuo ......................... 702/19 |
| 6,280,396 B1 * | 8/2001 | Clark .......................... 600/547 |

FOREIGN PATENT DOCUMENTS

| | | |
|---|---|---|
| EP | 0 926 488 | 6/1999 |
| JP | 10-96706 | 4/1998 |
| JP | 10333778 | 12/1998 |
| JP | 11-19059 | 1/1999 |
| JP | 11244253 | 9/1999 |

* cited by examiner

Primary Examiner—Max F. Hindenburg
Assistant Examiner—Pamela Wingood
(74) Attorney, Agent, or Firm—McDermott, Will & Emery

(57) ABSTRACT

Disclosed is an improvement in a living body variable measuring device comprising: a power supply; an inputting unit for inputting physical data of individuals whose body variables are to be measured; a memory device for storing the physical data of individuals thus inputted; a bioelectrical impedance gauge; an arithmetic operation-and-control unit for determining the living condition of each individual from the bioelectrical impedance and the personal physical data; and a display for displaying the result of the arithmetic operation and other pieces of information. It further comprises a lid for covering the body of said measuring device. The lid is equipped with a switch responsive to the opening of the lid for turning said power supply on.

3 Claims, 7 Drawing Sheets

COMPACT TYPE OF LIVING BODY VARIABLE MEASURING DEVICE

BACKGROUND OF THE INVENTION

1. Field of the Invention

The present invention relates to a device for measuring some living body variables such as body fat, muscle quantity or body water content, and more particularly to the geometrical shape of such a measuring device.

2. Prior Art

Recently people have been concerned with their health. Accordingly a variety of gauges permitting people to obtain blood pressure, pulsation and other pieces of information pertaining to their health are commercially available. From the point of health monitoring view the body fat percentage rather than body weight has been increasingly of concern. In the hope of meeting such need a body fat monitor for estimating the body fat quantity in terms of bioelectrical impedance was proposed. Such body fat monitors have been popular now for home use because of facilitating the required measurement. The bioelectrical impedance can be determined by making an electric current to flow between two selected points in the body and by measuring the voltage appearing therebetween. The body fat percentage or body fat quantity can be determined from the so determined bioelectrical impedance and from the height, weight, sex, age and other personal particulars, and the so determined variables are shown on the display. It is said that the probability with which fattish people suffer from life-style related diseases is larger. Nowadays, not only old people but also young people who are concerned with their health use body fat monitors to check how their fat percentage has been varying.

Weight scales each equipped with a body fat monitor are actually used. Japanese Patent Application Laid-Open No.11-19059 proposed a portable type of card-like gauge. Now, such gauges are commercially available in the market, and can be carried and used anywhere as for instance follows: the required measurements are effected before and after taking a certain internal combustion-causing exercise such as walking or jogging to realize how much the body fat has been reduced. For another example the body water content is determined in terms of the bioelectrical impedance while taking an exercise, thus meeting the need of monitoring how the body water content is varying while taking the exercise; such monitoring is supposed to be of great concern depending on what kind of exercise is being taken.

Small-sized body fat percentage gauges of the above-mentioned type (see Japanese Patent Application Laid-Open No.11-19059) have their parts such as display, power switch and measurement electrodes exposed on their front side. Thus it may be possible that the power switch be inadvertently touched to cause it to turn on while taking an exercise, thus wasting a significant amount of electric power and accordingly shortening the battery life. Outdoor exercises such as jogging or walking are apt to collect dust on the measurement electrodes of the gauge, causing errors in measuring bioelectrical impedance, and hence body fat percentage.

The display may be an LCD using a glass plate, which can be broken if the gauge inadvertently falls on the ground while taking an exercise.

SUMMARY OF THE INVENTION

In view of the above one object of the present invention is to provide a small-sized measuring device permitting required measurements of living body variables such as body fat percentage, body water content or muscle quantity to be effected anywhere, the measuring device being guaranteed to be free of the inadvertent switching-on of the power switch and contamination of the measurement electrodes with dust, preventing the fragile display from being broken.

To attain this object a living body variable measuring device comprising: an electric power supply; an inputting unit for inputting physical data of individuals whose body variables are to be measured; a memory device for storing the physical data of individuals thus inputted; electrodes for use in measuring the living body variable; an arithmetic operation-and-control unit for determining the living condition of each individual from the living body variable and the personal physical data; and a display for displaying the result of the arithmetic operation and other pieces of information, is improved according to the present invention in that it further comprises a lid for covering the body of said measuring device.

The measuring device further comprises an electric power switch, which is responsive to the opening and closing of said lid for turning said electric power supply on and off respectively.

Said display may be mounted to the inside of said lid.

Said display may be mounted to the upper surface of the body of said measuring device.

Said inputting unit may be provided on the upper surface of the body of said measuring device.

The voltage measuring electrodes of said electrodes may be provided on the upper surface of the body of said measuring device to be covered by said lid when closed.

All of the voltage measuring electrodes and current feeding electrodes may be provided on the upper surface of the body of said measuring device to be covered by said lid when closed.

One paired set of said electrodes may be provided on the upper surface of the body of said measuring device; the other paired set of said electrodes may be provided on the inside of said lid; and said lid may be a hinged cover which is rotatable 360 degrees about the hinge.

A living body variable measuring device comprising: an electric power supply; electrodes for use in measuring the living body variable and inputting physical data of individuals whose body variables are to be measured; a memory device for storing the physical data of individuals thus inputted; an arithmetic operation-and-control unit for determining the living condition of each individual from the living body variable and the personal physical data; and a display for displaying the result of the arithmetic operation and other pieces of information, is improved according to the present invention in that it further comprises a lid for covering the body of said measuring device.

A living body variable measuring device comprising: an electric power supply; electrodes for use in measuring the living body variable; a touch-sensitive LCD for use in inputting physical data of individuals whose body variables are to be measured; a memory device for storing the physical data of individuals thus inputted; and an arithmetic operation-and-control unit for determining the living condition of each individual from the living body variable and the personal physical data, the result of the arithmetic operation being displayed by said touch-sensitive LCD, is improved according to the present invention in that it further comprises a lid for covering the body of said measuring device.

Other objects and advantages of the present invention will be understood from the following description of living body variable measuring device according to some preferred embodiments of the present invention, which are shown in the accompanying drawings.

DESCRIPTION OF PREFERRED EMBODIMENTS

Figure 1:
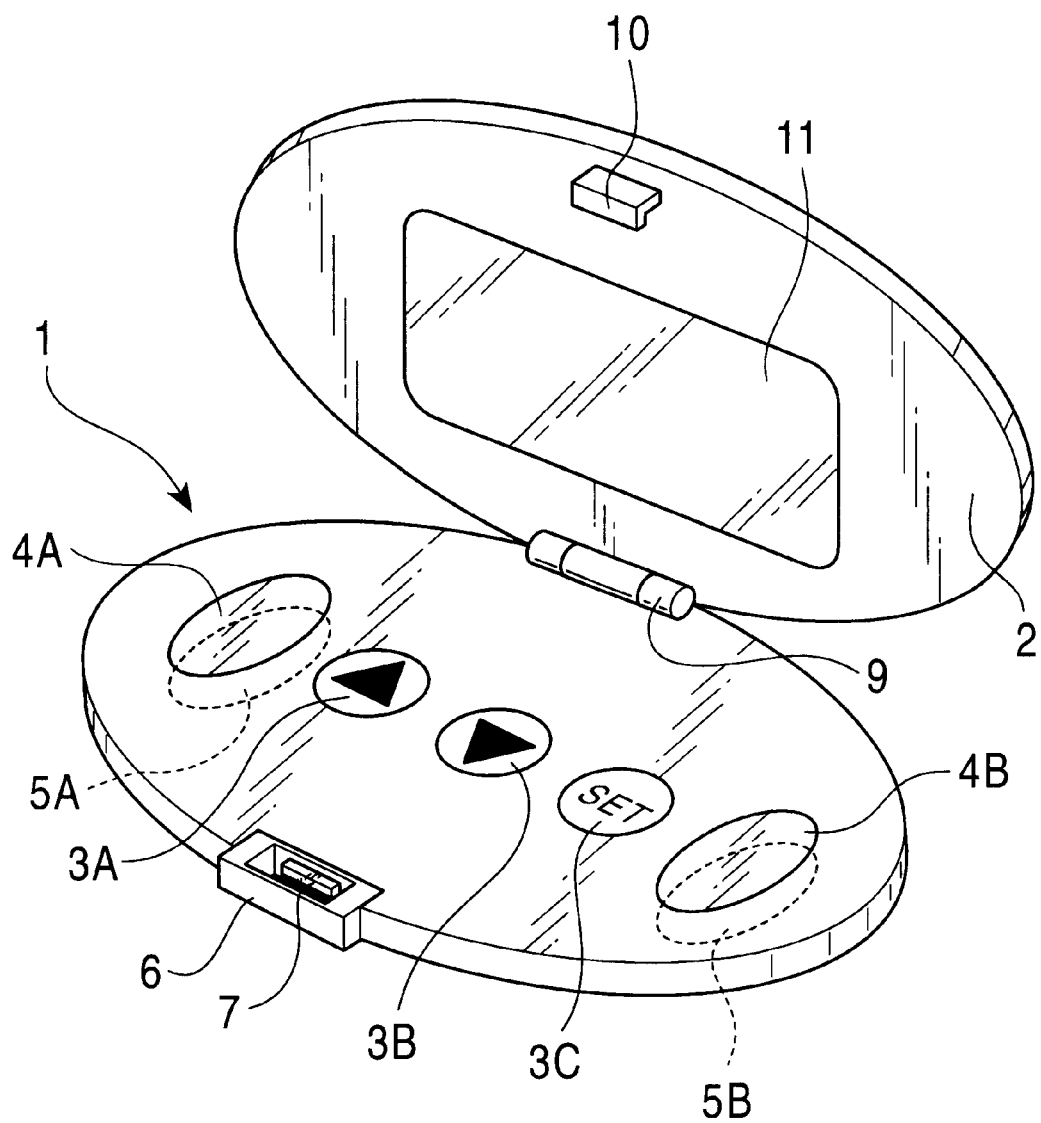
FIG. 1 is a schematic external view of a body fat monitor according to a first embodiment.
Figure 2:
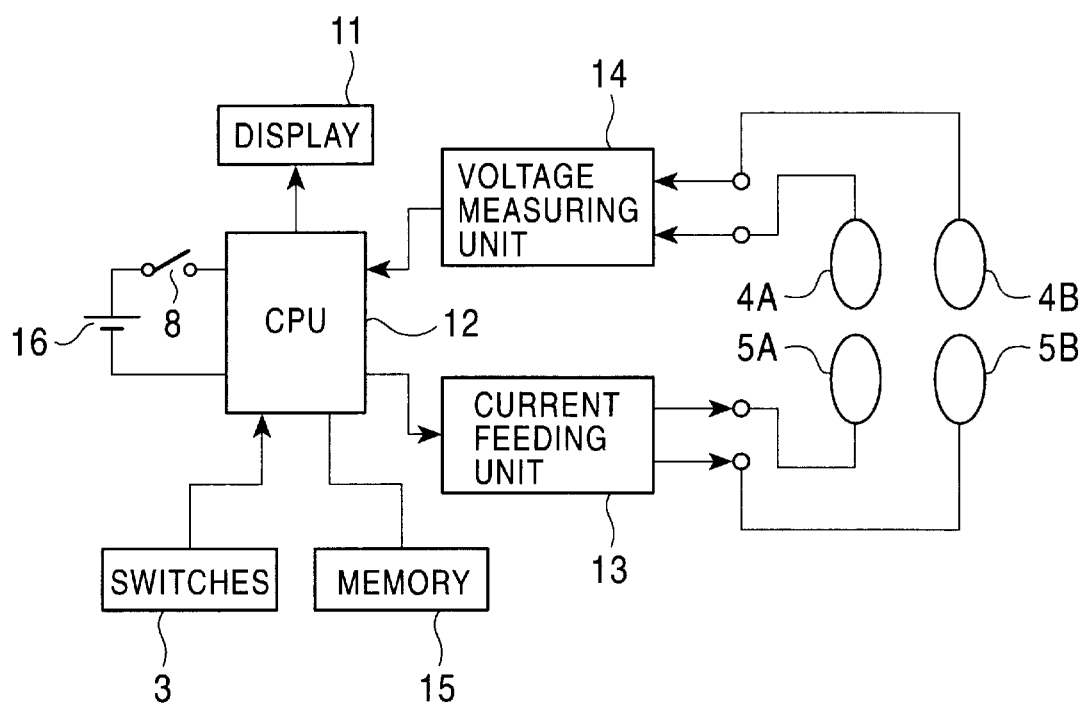
FIG. 2 is a block diagram of the body fat monitor of FIG. 1.

FIG. 1 shows a living body variable measuring device according to the first embodiment. It looks like an elliptical compact, and it is shown with its lid or hinged cover 2 opening upright at right angle relative to the upper surface of the gauge body. A plurality of inputting push buttons 3A and 3B and a setting push button 3C appear on the upper surface of the gauge body. The figure appearing on the display 11 will increase one by one every time the "UP" push button 3A is depressed whereas the figure appearing on the display 11 will decrease one by one every time the "DOWN" push button 3B is depressed. When entering selected pieces of information, the setting button 3C is depressed to start and terminate the recording of such data. Voltage measuring electrodes 4A and 4B appear on the right and left sides of the upper surface of the gauge body. The gauge body has current feeding electrodes 5A and 5B provided on the backside of the gauge body in the confronting relation with the voltage measuring electrodes 4A and 4B.

A push button 6 is slidably attached to the front edge of the gauge body. It can move back and forth, and it has a recess made on its upper surface. Specifically the recess has a catch 7 formed on its rear side, and a power supply switch 8 is installed in the recess.

The lid 2 is so made that it may cover the upper surface of the gauge body, and its rear edge is rotatably jointed to the gauge body with a hinge 9. The lid 2 has an L-shaped projection 10 formed on its front edge. The projection 10 is positioned in confronting relation relative to the hinge 9 and the catch 7 in the recess of the push button 6. When the lid 2 is closed, the projection 10 is caught by the catch 7 in the recess of the push button 6. The lid 2 cannot be opened without depressing the push button 6. In closing position the power supply switch 8 is pressed by the projection 10, thereby putting the switch 8 in the "off"-position. When the lid 2 is opened, the power supply switch 8 turns on, thus putting the body fat monitor on standby.

The display 11 fixed to the rear side of the lid 2 shows personal particulars, the results of the measurements and other useful pieces of information.

The body fat monitor 1 has a CPU 12 installed in its body, and the CPU 12 is connected to the inputting and setting push buttons 3A, 3B and 3C, the display 11, functioning as an arithmetic operation-and-control unit. The CPU 12 is connected to a current feeding unit 13 for permitting an electric current to flow in the body via the current feeding electrodes 5A and 5B, and is connected to a voltage measuring unit 14 for measuring the voltage appearing between the voltage measuring electrodes 4A and 4B. Also, the CPU 12 is connected to a memory 15 for storing physical data inputted by the inputting buttons 3A, 3B and 3C, and is connected to a battery 16 via the electric power supply switch 8.

Figure 3:
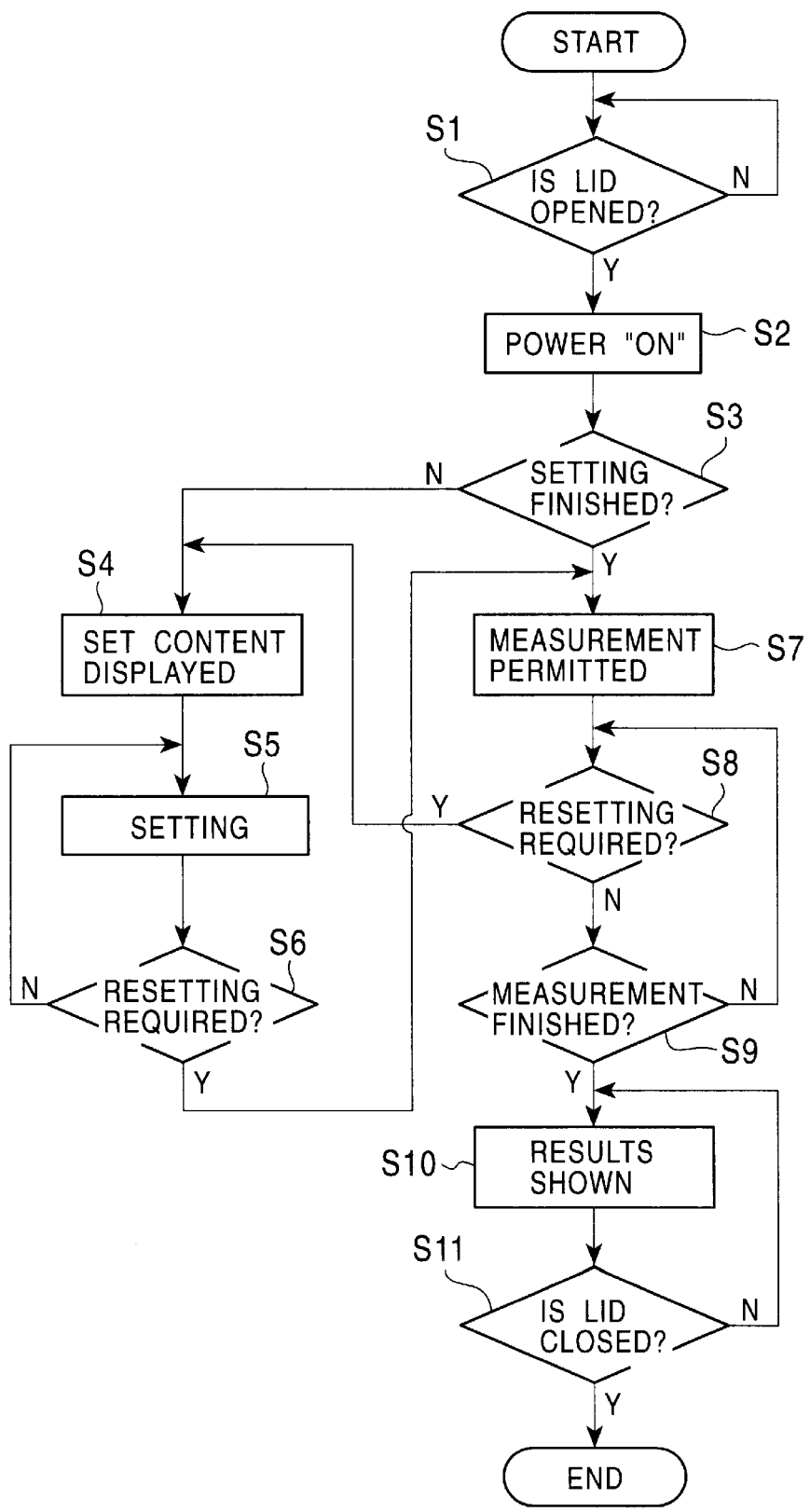
FIG. 3 is a flow chart showing a series of actions taken for measuring the body fat.

Referring to FIG. 3, a series of actions taken in measuring the body fat are described below: the lid 2 is closed, and the electric power supply switch 8 turns off, disconnecting the gauge circuit from the electric power supply 16.

When the lid 2 is opened (STEP S1), the electric power supply switch 8 turns on, connecting the CPU 12 to the battery 16, putting the body fat monitor 1 on standby (STEP S2). The user can adjust the angle which the lid 2 forms relative to the upper surface of the gauge body 1 so that the user may look at the display 11 with ease.

When the power supply turns on, the CPU 12 makes a decision as to whether or not the physical data of the user have been stored in the memory 15 (STEP S3). If such data have been recorded, the required measurement is allowed to start immediately. If not, the gauge will be put in condition for recording such personal data, while presenting on the display a message inducing the user to enter such data (STEP S4).

Then, the user inputs the height, weight, sex, age and other pieces of physical information one after another by changing the figure or word on the display 11 with the "UP" push button 3A and the "DOWN" push button 3B and by recording a desired figure or word when reached with the setting push button 3C. Then, the contents thus recorded appear on the display 11 (STEP S5). When the setting push button 3C is depressed, the subsequent item to enter appears on the display 11, so that the user may input the personal data in a similar way. Finally all personal data have been recorded in the memory 15, finishing the required setup (STEP S6). Thus, the body fat gauge is now on standby for measurement.

In the standby condition the contents of personal data stored in the memory 15 and a message inducing the user to start measurement are given on the display 11. At this stage, if the user is going to make a modification on the personal data already recorded, he pushes the setting button 3C (STEP S8), allowing the proceeding to go to STEP S4.

Figure 4:
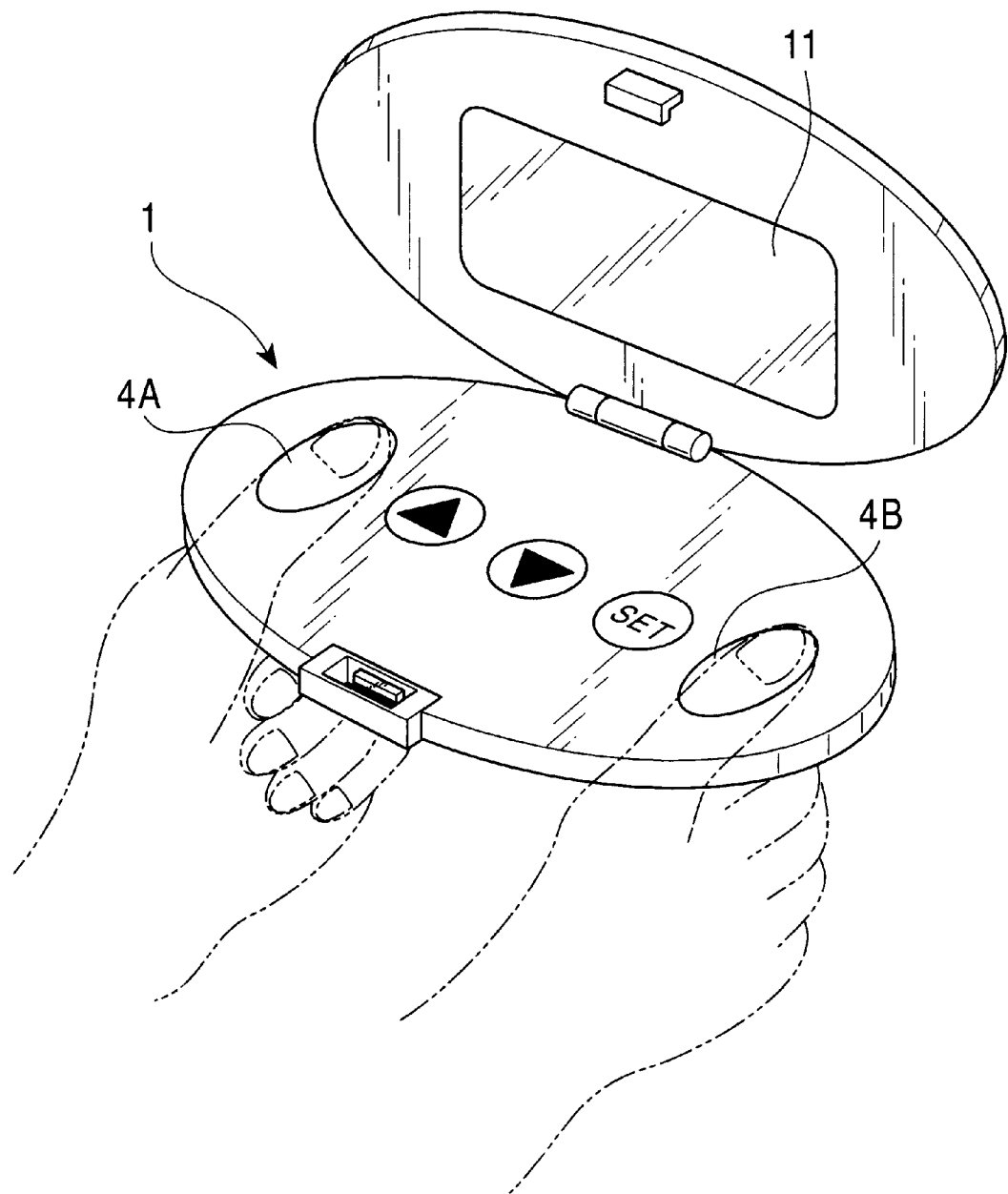
FIG. 4 is a perspective view of the body fat monitor of FIG. 1, showing how it is used.

At STEP S8 the user does not depress the setting button 3C, and then, as shown in FIG. 4, the measurement can be made to start by putting his thumbs on the opposite voltage measuring electrodes 4A and 4B and by putting his index fingers on the current feeding electrodes 5A and 5B, which are on the rear side of the gauge body 1. The user continues to hold this position until the value of bioelectrical impedance appears on the display 11. Specifically the CPU 12 executes the calculation of the body fat on the basis of the personal data and the bioelectrical impedance (STEP S9). The results of calculation are given on the display 11 (STEP S10). Closure of the lid 2 is detected in terms of whether the electric power supply 8 turns off (STEP S81). Appearance of the results of calculation on the display 11 continues until the lid 2 is closed. When the lid 2 is closed, the electric power supply turns off, thus disconnecting the gauge circuit from the electric power supply to put the same in dormant condition.

Figure 5:
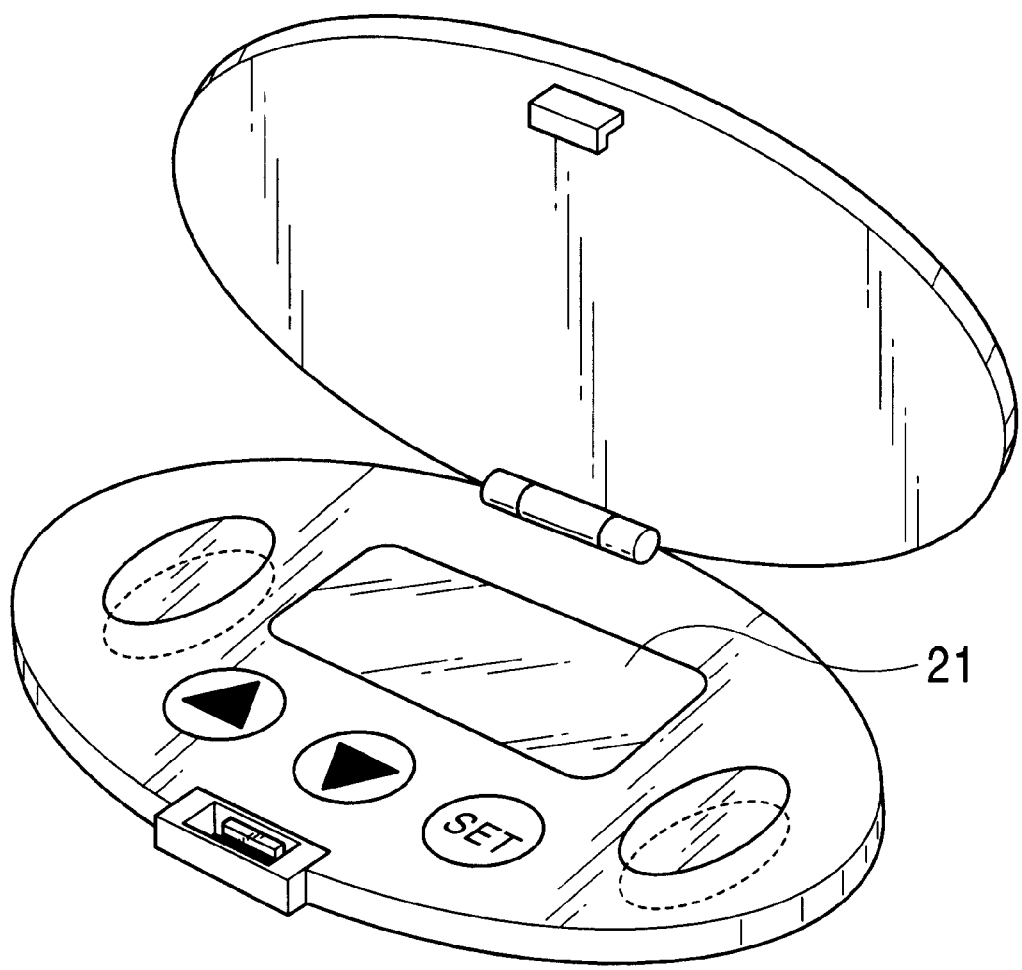
FIG. 5 is a perspective view of a living body variable measuring device according to a second embodiment.

FIG. 5 shows a living body variable measuring device according to the second embodiment. As shown, the measuring device has a display provided on its body, thus eliminating the necessity of extending electric wires inside of the hinge to reach the display on the lid as in the first embodiment. Accordingly the hinge structure is less complicated, and its strength is increased to be resistive against the impact caused by falling on the ground.

Figure 6:
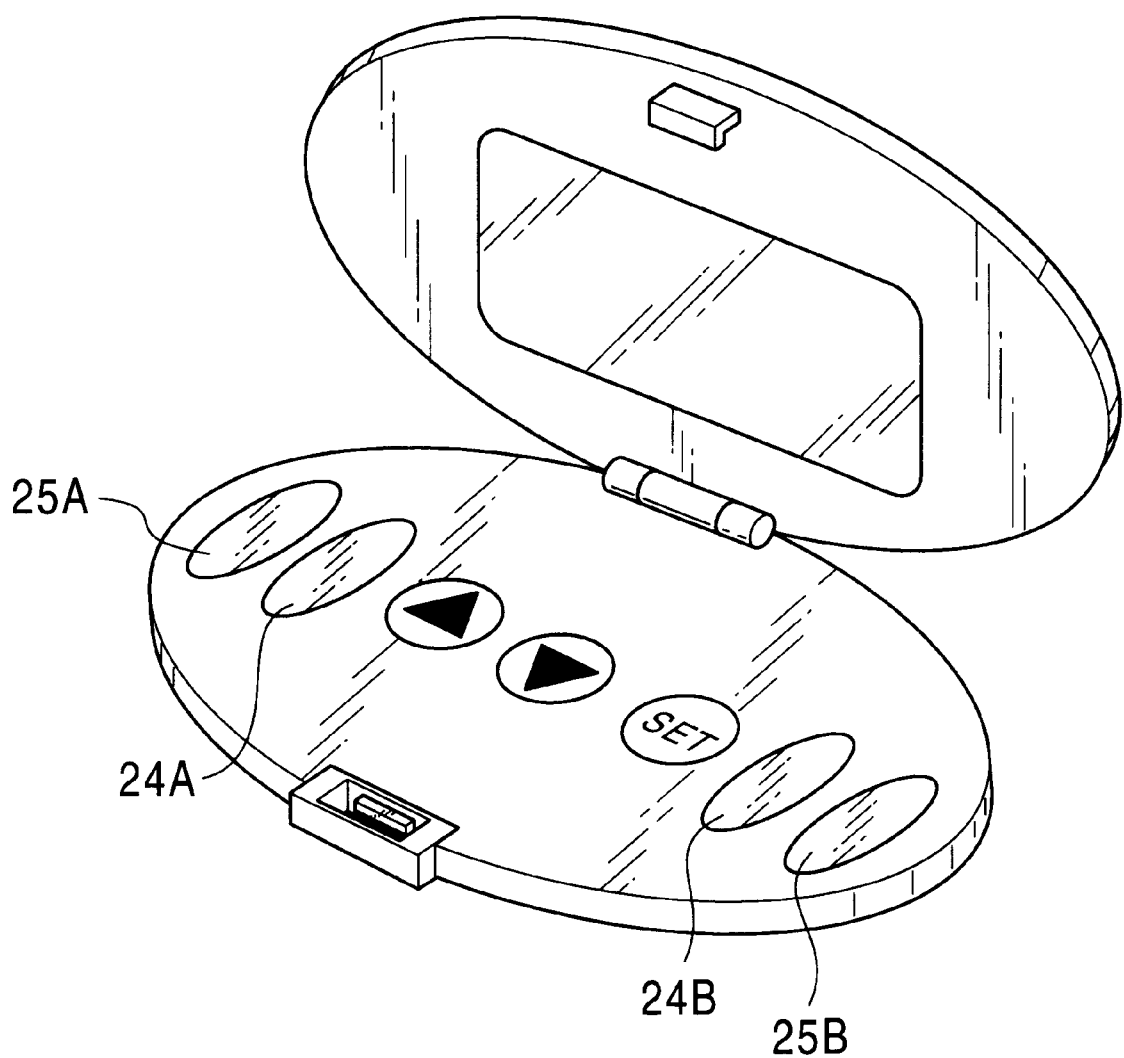
FIG. 6 is a perspective view of a living body variable measuring device according to a third embodiment.

FIG. 6 shows a living body variable measuring device according to the third embodiment. As shown, the measuring device has its voltage measuring and current feeding electrodes 24A, 24B and 25A and 25B provided on the upper surface of the gauge body. Thus, when being not used, all electrodes are covered by the lid, thus preventing them from being contaminated with dust while the user takes an exercise, assuring that a required measurement be effected with accuracy.

Figure 7A:
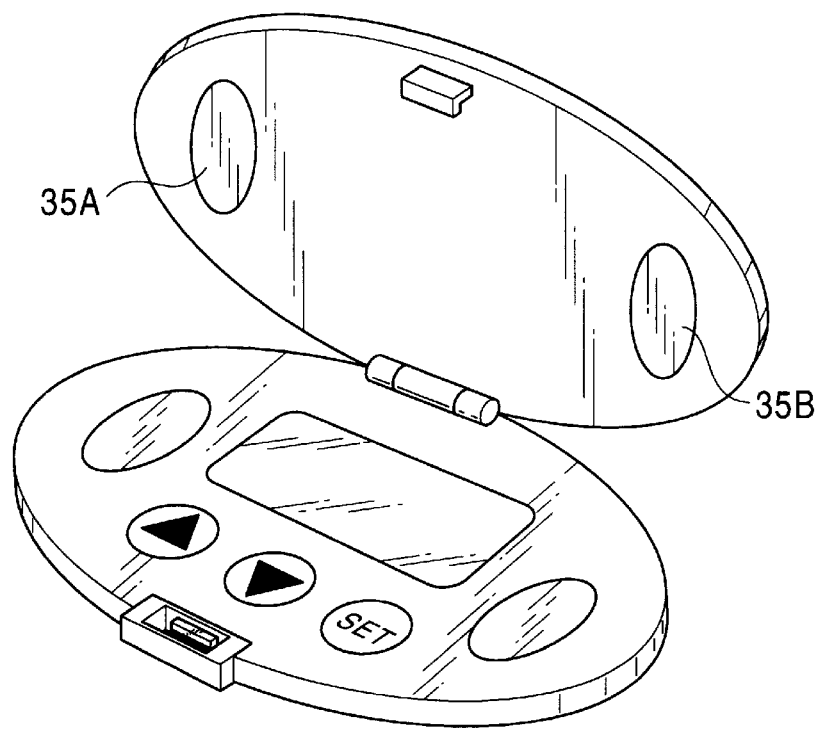
FIGS. 7(a) and 7(b) are perspective views of a living body variable measuring device according to a fourth embodiment, showing the measuring device with its lid opened and closed respectively.
Figure 7B:
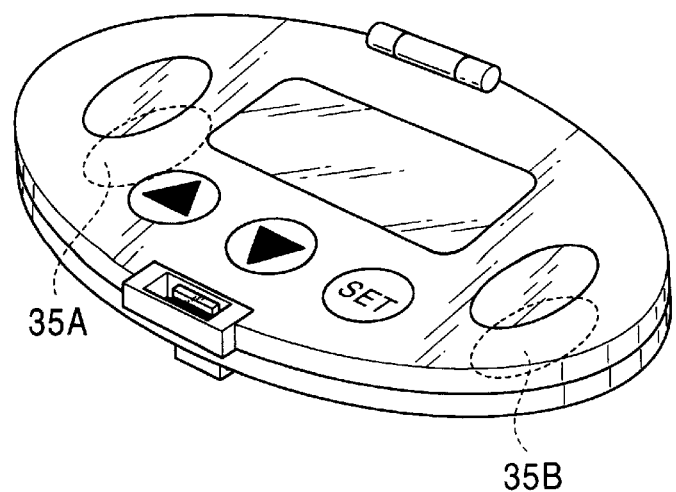

FIG. 7 shows a living body variable measuring device according to the fourth embodiment. As shown in FIG. 7(a), the measuring device has a 360 degree-rotatable lid hinged to its body, and the lid has current feeding electrodes 35A and 35B provided thereon. FIG. 7(b) shows the body fat monitor with its lid turning back on the rear side of the gauge body. In this position it has the same electrode arrangement as in the first embodiment of FIG. 1. A required measurement can be effected by putting one's fingers on the electrodes in the same way as in the first embodiment. Advantageously the user can effect a required measurement while assuming the natural, less-laborious finger-pinching position on the gauge. Contamination of electrodes can be prevented while the user takes an exercise, assuring that a required measurement be effected with accuracy.

In the body fat measuring devices as described above a number of push buttons 3A, 3B and 3C are used in entering the height, weight, sex, age and other personal data. Instead, the voltage measuring electrodes 4A and 4B and current feeding electrodes 5A and 5B may be so modified that they may have same switching functions as such push buttons 3A, 3B and 3C. Thus, the keyless structure results.

In the above described measuring devices the push buttons 3A, 3B and 3C are used along with the LCD 11. Alternatively use is made of an inputting-and-displaying type of LCD which is responsive to a touch on a selected segment on its front plate. Specifically a number of switch images appear on the LCD, allowing the user to touch a selected switch image for inputting a required piece of information. Use of such touch-sensitive LCD permits the number of parts to be reduced, and the limited space available on the upper surface of the gauge body and inside surface of the lid can be effectively used.

The present invention is described as being applied to a body fat monitor, but it can be equally applied to any living body variable measuring device such as muscle quantity or body water content measuring devices.

What is claimed is:

1. A compact type of living body variable measuring device comprising:
    an inputting device;
    a memory device;
    electrodes;
    an arithmetic operation-and-control unit;
    a lid for covering a body of the measuring device;
    an electric power switch responsive to the opening and closing of said lid for turning an associated electric power supply on and off respectively; and
    a display device, in which:
        said inputting device inputs physical data of individuals whose body variables are to be measured;
        said memory device stores said physical data of individuals thus inputted;
        said electrodes are used in measuring the living body variable;
        said arithmetic operation-and-control unit determines the living condition of each individual from the living body variable and the personal physical data;
        said display device displays the result of the arithmetic operation and other pieces of information,
        wherein one paired set of said electrodes are provided on the upper surface of the body of said measuring device; the other paired set of said electrodes are provided on the inside of said lid; and said lid is a hinged cover which is rotatable approximately 360 degrees about the hinge.

2. A compact type of living body variable measuring device comprising: a memory device, electrodes, an arithmetic operation-and-control unit and a display device, in which:
    said electrodes are used in measuring the living body variable and inputting physical data of individuals whose body variables are to be measured;
    said memory device stores said physical data of individuals thus inputted;
    said arithmetic operation-and-control unit determines the living condition of each individual from the living body variable and the personal physical data; and
    said display displays the result of the arithmetic operation and other pieces of information,
    characterized in that it further comprises a lid for covering the body of said measuring device.

3. A compact type of living body variable measuring device comprising:
    an inputting device;
    a memory device;
    electrodes;
    an arithmetic operation-and-control unit;
    a display device;
    a lid; and
    an electric power switch, in which:
        said inputting device inputs physical data of individuals whose body variables are to be measured;
        said memory device stores said physical data of individuals thus inputted;
        said electrodes are used in measuring the living body variable, one paired set of said electrodes being provided on the upper surface of the body of said measuring device and another paired set of said electrodes are provided on the inside of said lid;
        said arithmetic operation-and-control unit determines the living condition of each individual from the living body variable and the personal physical data; and
        said display device displays the result of the arithmetic operation and other pieces of information,
        said lid is a hinged cover which is rotatable approximately 360 degrees about the hinge to cover a body of said measuring device when closed; and
        said electric power switch is responsive to the opening and closing of said lid for turning an associated electric power supply on and off respectively.

* * * * *